United States Patent
Lee et al.

(10) Patent No.: US 10,470,845 B2
(45) Date of Patent: Nov. 12, 2019

(54) DISPENSER DEVICE FOR DENTAL MATERIAL

(71) Applicant: B&L BIOTECH, INC., Ansan-si, Gyeonggi-do (KR)

(72) Inventors: In Whan Lee, Seoul (KR); Seung Ki Baek, Seoul (KR); Gil Hwan Sung, Seoul (KR); In Jeong Choi, Seoul (KR)

(73) Assignee: B&L BIOTECH, INC., Ansan-si (KR)

( * ) Notice: Subject to any disclaimer, the term of this patent is extended or adjusted under 35 U.S.C. 154(b) by 0 days.

(21) Appl. No.: 15/080,912

(22) Filed: Mar. 25, 2016

(65) Prior Publication Data

US 2017/0049533 A1    Feb. 23, 2017

(30) Foreign Application Priority Data

Aug. 17, 2015  (KR) .................. 10-2015-0115367

(51) Int. Cl.
*A61C 5/55*  (2017.01)
*A61C 5/62*  (2017.01)

(52) U.S. Cl.
CPC . *A61C 5/55* (2017.02); *A61C 5/62* (2017.02)

(58) Field of Classification Search
CPC .... A61C 5/62; A61C 5/66; A61C 5/55; A61C 5/60–68; A61C 9/0026; B05B 17/00; B05B 17/001; B05B 17/00523; B05B 17/00526; B05C 17/00; B05C 17/001; B05C 17/00523; B05C 17/00526;

(Continued)

(56) References Cited

U.S. PATENT DOCUMENTS

| 5,236,269 A | * | 8/1993 | Handy | ................ B05C 17/0053 |
| | | | | 219/227 |
| 5,664,701 A | * | 9/1997 | Massena | ........... B05C 17/00526 |
| | | | | 219/227 |

(Continued)

FOREIGN PATENT DOCUMENTS

| EP | 0 619 987 A2 | 10/1994 |
| JP | 2002153491 A | 5/2002 |

(Continued)

OTHER PUBLICATIONS

Birk Manufacturing. "Kapton Heaters". Dec. 3, 2012.*

(Continued)

*Primary Examiner* — Edward Moran
(74) *Attorney, Agent, or Firm* — Sughrue Mion, PLLC (57) ABSTRACT

Disclosed is a dispenser device for dental material, the dispenser device including a body, a capsule configured to detachably couple with the body, and to accommodate a dental material, a piston configured to pressurize the capsule and to discharge the dental material from the capsule, an actuator configured to actuate the piston, and a heating unit provided to the body, and configured to locally heat the capsule. The heating unit includes a film heater configured to generate heat for heating the capsule provided to the body, and a heat transferor provided between the capsule and the film heater, configured to transfer the heat generated from the film heater to the capsule, and formed using a metal material.

6 Claims, 4 Drawing Sheets

(58) Field of Classification Search
CPC ......... B05C 1/003; B05C 3/005; B05C 5/001;
B05C 9/14; B05C 17/01; B05C 17/00546
USPC ....... 222/146.2, 146.5, 325–327, 386; 401/1,
401/2; 604/6.13, 113, 291
See application file for complete search history.

(56) References Cited

U.S. PATENT DOCUMENTS

| | | | |
|---|---|---|---|
| 5,743,431 A * | 4/1998 | Brattesani | A61C 5/62 222/1 |
| 2002/0058231 A1 * | 5/2002 | Friedman | A61C 5/62 433/90 |
| 2009/0191505 A1 * | 7/2009 | Clark | A61C 5/50 433/39 |
| 2011/0165537 A1 | 7/2011 | Jung et al. | |
| 2015/0079538 A1 | 3/2015 | Li et al. | |

FOREIGN PATENT DOCUMENTS

| | | |
|---|---|---|
| JP | 2009082791 A | 4/2009 |
| JP | 2010193941 A | 9/2010 |
| KR | 1020060122195 A | 11/2006 |
| KR | 1020100006112 A | 1/2010 |
| KR | 1020130008254 A | 1/2013 |

OTHER PUBLICATIONS

Stopperan, "Understanding Etched Foil Flexible Heaters". May 4, 2012 (Year: 2012).*
Communication dated Jan. 9, 2017 from the German Patent Office in corresponding German Patent Application No. 102016106019.4.
Communication dated Jan. 24, 2017 from the Japanese Patent Office in corresponding Japanese Patent Application No. 2016-074171.
Communication dated Dec. 11, 2015 from the Korean Patent Office in corresponding Korean Patent Application No. 10-2015-0115367.
Communication dated Sep. 26, 2017 from the Japanese Patent Office in corresponding Japanese Patent Application No. 2016-074171.

* cited by examiner

DISPENSER DEVICE FOR DENTAL MATERIAL

CROSS-REFERENCE TO RELATED APPLICATION

This application claims the priority benefit of Korean Patent Application No. 10-2015-0115367, filed on Aug. 17, 2015, in the Korean Intellectual Property Office, the disclosure of which is incorporated herein by reference.

BACKGROUND

1. Field of the Invention

Example embodiments relate to a dispenser device for dental material, and more particularly, to a dispenser device for dental material that may heat a capsule accommodating a dental material, such as resin and the like, using a film heater, and may discharge the dental material from the capsule.

2. Description of the Related Art

In general, a dental restoration material requires relatively great strength to restore a chewing function. Thus, materials such as gold, alloy, amalgam, and the like, have been typically used for the dental restoration material. Such metal materials may not be aesthetic due to a lack of a tooth color. Further, it may be very awkward to see a metal from a front tooth and a person may leave a less favorable impression. Also, since a metal material does not couple with a tooth, a relatively large portion of the tooth is to be cut to prevent an elimination of a restoration material.

On the contrary, an adhesive restoration method using resin may perform minimal cutting of a tooth and may strengthen a tooth structure that has become weak due to a tooth defect. That is, instead of performing redundant tooth cutting, a tooth may be maintained using a preserving method.

Resin refers to a mixed material that includes organic polymer and inorganic filler. Currently, resin is gaining attention as a dental restoration material.

To fill a dental restoration material, such as resin, in a tooth, a dental filling device and a dental dispenser for discharging the dental restoration material are required. The dental dispenser device may include a heater capable of heating the dental restoration material in order to effectively discharge the dental restoration material.

SUMMARY

Example embodiments provide a dispenser device for dental material that may discharge a dental material from a capsule by locally heating the capsule, accommodating the dental material, using a film heater in order to extrude the dental material such as resin having a relatively high viscosity.

According to an aspect of example embodiments, there is provided a dispenser device for dental material, the dispenser device including a body, a capsule configured to detachably couple with the body, and to accommodate a dental material, a piston configured to pressurize the capsule and to discharge the dental material from the capsule, an actuator configured to actuate the piston, and a heating unit provided to the body, and configured to locally heat the capsule. The heating unit may include a film heater configured to generate heat for heating the capsule provided to the body, and a heat transferor provided between the capsule and the film heater, configured to transfer the heat generated from the film heater to the capsule, and formed using a metal material.

Also, the film heater may be formed using a flexible material in a shape of a thin plate.

Also, the film heater may be configured to couple with the body in a bent state as a curved surface.

Also, the film heater may be formed using a polyimide material.

Also, the film heater may be configured to contact with the heat transferor, and to transfer heat to the heat transferor in a conductive manner, and the heat transferor may be in contact with a portion of the capsule, and configured to locally heat the capsule.

Also, a capsule combining groove through which the capsule is to couple with the body may be formed at a front end of the body to be in a dented form, and a heat transferor inserting hole via which the heat transferor is inserted into the body may be formed in the capsule combining groove using a puncturing.

Also, the heat transferor may be provided below the capsule, and the film heater is provided below the heat transferor.

Also, the dispenser device for dental material may further include a cover configured to cover the film heater, and to detachably couple with the body.

Also, the dental material accommodated in the capsule may include at least resin.

According to another aspect of example embodiments, there is provided a dispenser device for dental material, the dispenser device including a capsule configured to accommodate a dental material, a body including a capsule combining groove through which the capsule is to detachably couple with the body, a film heater provided to the capsule combining groove, and configured to locally heat at least a portion of the capsule, and a discharge unit configured to pressurize the capsule, and to discharge the dental material from the capsule.

Also, the dispenser device for dental material may further include a heat transferor provided between the capsule and the film heater, configured to transfer heat generated from the film heater to the capsule, and formed using a metal material.

Other features and aspects will be apparent from the following detailed description, the drawings, and the claims.

Effects of Invention

According to example embodiments, a film heater of a flexible material is used to heat a dental material having a relatively viscosity, instead of a conventional heating pipe and nicrome wire. Accordingly, it is possible to readily mount a heater regardless of a shape, a size, and a structure of a portion to which the heater is provided.

Also, according to example embodiments, it is possible to further advantageously maintain a temperature and to achieve an enhanced use convenience compared to a conventional method of using a heating block.

Also, according to example embodiments, since an inner structure of a dispenser device for dental material is simplified, a manufacture and processing may be conveniently performed.

Also, according to example embodiments, a pressure and a temperature of a dental material, such as resin and the like, may uniformly increase over time instead of instantaneously increasing by locally heating a lower end of a capsule, such as a resin capsule and the like, that accommodates the dental material. Also, the dental material, such as resin and the like, accommodated in the capsule may not be deformed.

Also, according to example embodiments, it is possible to relatively enhance the battery efficiency by locally heating a capsule that accommodates a dental material using a film heater.

Also, according to example embodiments, it is possible to readily attach and detach a capsule that accommodates a dental material, to and from a dispenser device.

Also, according to example embodiments, since a structure of a portion for heating a capsule is simplified, a risk of short-circuit and damage may be reduced, thereby further enhancing a stability.

Also, according to example embodiments, the capsule has a curved outer surface, the heat transferor has a curved upper surface and a lower surface, and wherein the curved surface of the capsule combining groove corresponds to and surrounds the curved upper surface of the heat transferor. Additionally, the heat transferor is provided between the capsule and the film heater such that the curved upper surface of the heat transferor is in direct contact with a portion of the curved outer surface of the capsule and the curved surface of the capsule combining groove surrounding the curved surface of the heat transferor is in direct contact with another portion of the curved outer surface of the capsule.

BRIEF DESCRIPTION OF THE DRAWINGS

These and/or other aspects, features, and advantages of the invention will become apparent and more readily appreciated from the following description of embodiments, taken in conjunction with the accompanying drawings of which.

DETAILED DESCRIPTION

Hereinafter, example embodiments are described in detail with reference to the accompanying drawings. The following specific structural or functional descriptions are exemplary to merely describe the example embodiments, and the scope of the example embodiments is not limited to the descriptions provided in the present specification. Various changes and modifications can be made thereto by those of ordinary skill in the art. Like reference numerals in the drawings denote like elements, and a known function or configuration will be omitted herein.

It will be understood that when an element or layer is referred to as being "on" or "connected to" another element or layer, it can be directly on or connected to the other element or layer or through intervening elements or layers may be present. In contrast, when an element is referred to as being "directly on" or "directly connected to" another element or layer, there are no intervening elements or layers present. Like reference numerals refer to like elements throughout. As used herein, the term "and/or" includes any and all combinations of one or more of the associated listed items.

Unless indicated otherwise, a statement that a first layer is "on" a second layer or a substrate is to be interpreted as covering both a case where the first layer is directly contacts the second layer or the substrate, and a case where one or more other layers are disposed between the first layer and the second layer or the substrate.

The spatially-relative expressions such as "below", "beneath", "lower", "above", "upper", and the like may be used to conveniently describe relationships of one device or elements with other devices or among elements. The spatially-relative expressions should be understood as encompassing the direction illustrated in the drawings, added with other directions of the device in use or operation. Further, the device may be oriented to other directions and accordingly, the interpretation of the spatially-relative expressions is based on the orientation.

Figure 1:
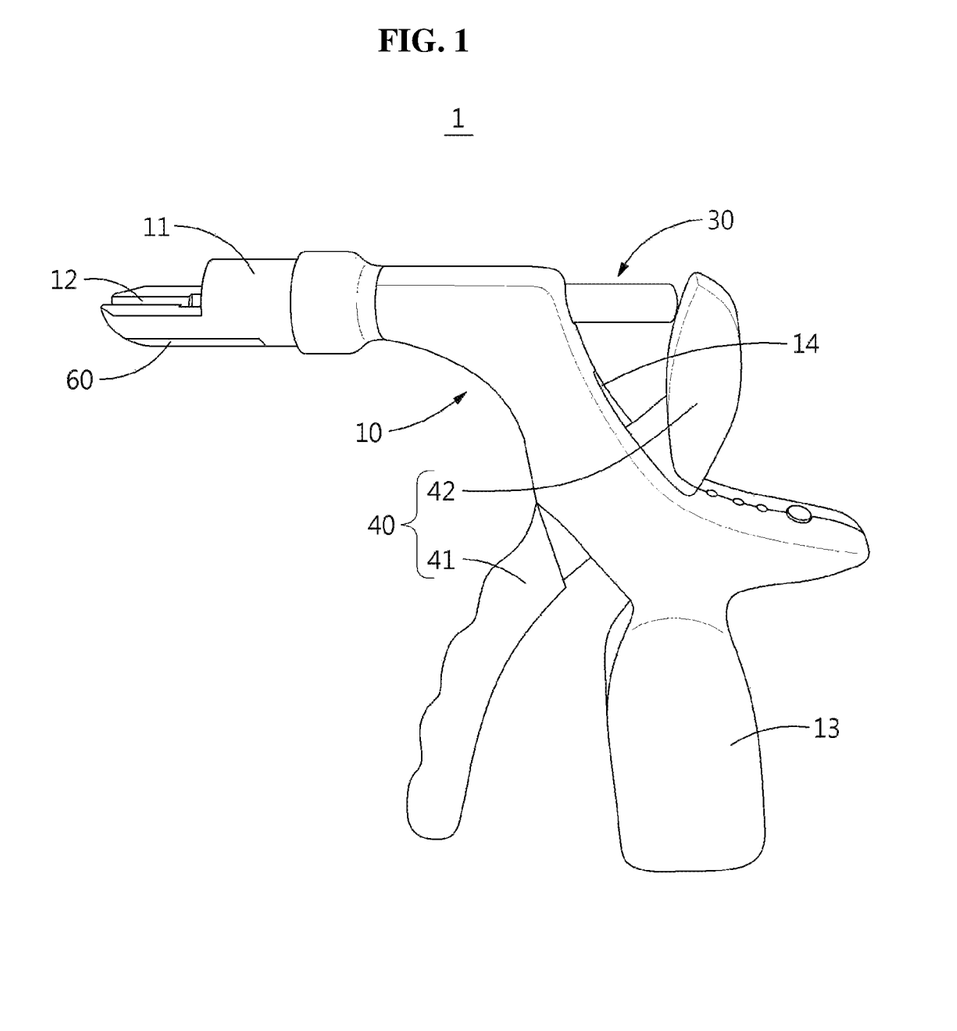
FIG. 1 is a perspective view of a dispenser device for dental material according to example embodiments.

FIG. 1 is a perspective view of a dispenser device for dental material (hereinafter, a dispenser device) according to example embodiments.

Referring to FIG. 1, the dispenser device 1 may include a body 10, a capsule 20, a piston 30, an actuator 40, and a heating unit 50.

The body 10 may be formed to have an overall gun shape, and may include a head 11 at a front end of the body 10 to detachably couple with the capsule 20. A capsule combining groove 12 through which the capsule 20 is to couple with the body 10 may be dented on one surface of the head 11.

A body grip 13 to be gripped by an operator with a hand may be provided at a lower portion of the body 10. A battery (not shown) may be provided in the body grip 13. In detail, the battery may be detachably accommodated in the body grip 13. For example, when the battery is discharged, the battery may be reusable by being easily separated from the body grip 13 and being charged. Further, the discharged battery may be replaced with a new fully charged battery.

Accordingly, without a connection of an electric wire for supplying electricity, the dispenser device 1 may wirelessly supply the electricity through the battery.

The battery may serve to supply power to the heating unit 50. The heating unit 50 will be described later.

The capsule 20 may detachably couple with the body 10 and a dental material may be accommodated in the capsule 20. A further description related to the capsule 20 will be made with reference to FIG. 5.

The piston 30 may serve to pressurize the capsule 20 to discharge a dental material from the capsule 20. In detail, a front end of the piston 30 may pass through a front portion of the body 10 and thereby be exposed in the capsule combining groove 12 formed on the head 11, and a rear end of the piston 30 may be partially exposed from an upper side of the body 10. A diameter of the front end of the piston 30 may be formed to be less than a diameter of the rear end of the piston 30.

Further, a piston combining hole 110 via which the piston 30 is receivable may be formed in an upper portion of the body 10.

The actuator 40 may serve to actuate the piston 30. The actuator 40 may include an actuator grip 41 arbitrarily operable by a user and a pressurizing portion 42 integrally formed with the actuator grip 41 and configured to pressurize the piston 30.

An actuator combining hole 14 via which the actuator 40 is to couple with the body 10 may be formed in a center portion of the body 10. The actuator combining hole 14 may be configured so that the actuator 40 may rotate within a predetermined angle range and to pressurize the piston 30.

In detail, in response to the user pulling the actuator grip 41 toward the body grip 13, the pressurizing portion 42 may push the rear end of the piston 30 so that the piston 30 may move forward straightly. That is, a moving direction of the actuator grip 41 and a moving direction of the pressurizing portion 42 may be opposite to each other, and the dental material may be discharged only in response to the pressurizing portion 42 pushing the piston 30. Accordingly, the piston 30 may move straight toward a front of the body 10 by the pressurizing portion 42, thereby discharging, from the capsule 20, the dental material accommodated in the capsule 20 that is coupled with the head 11. The piston 30 and the pressurizing portion 42 may discharge the dental material, for example, resin and the like, from the capsule 20 through interaction therebetween and thus, may be referred to as a discharge unit.

Figure 2:
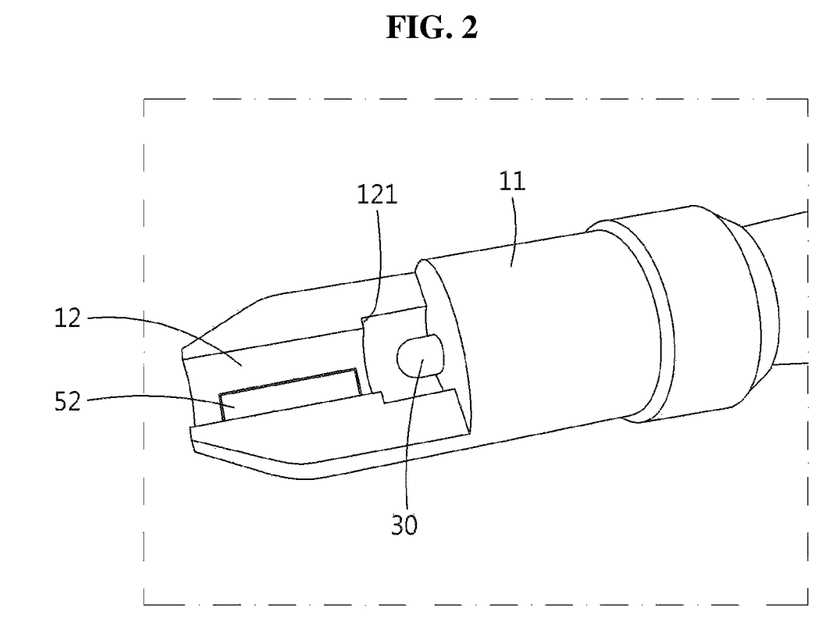
FIG. 2 is a view illustrating a state in which a heating unit is coupled with a head of a dispenser device for dental material according to example embodiments.
Figure 3:
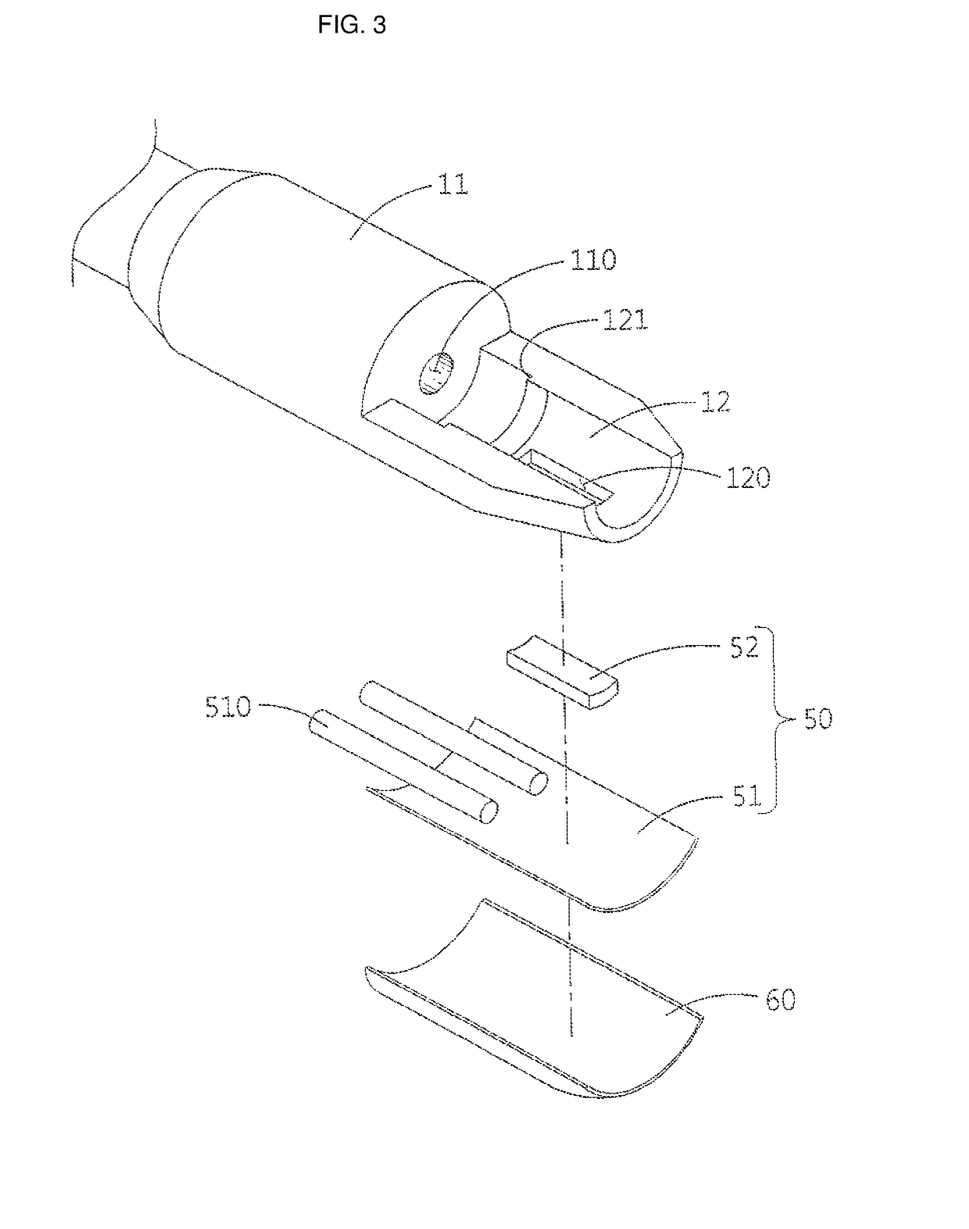
FIG. 3 is an exploded perspective view of a head, a heating unit, and a cover of a dispenser device for dental material according to example embodiments.
Figure 4:
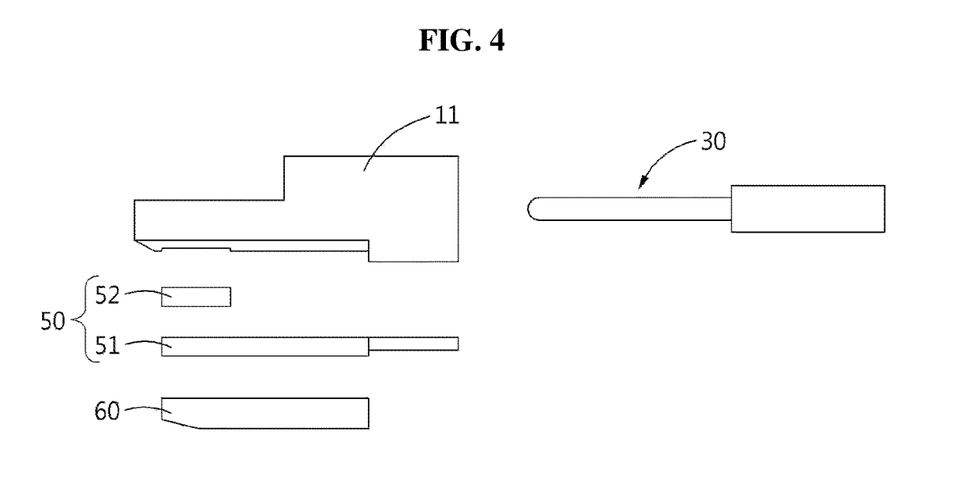
FIG. 4 is a cross-sectional view viewed at a side of a head, a heating unit, and a cover of a dispenser device for dental material according to example embodiments.

FIG. 2 is a view illustrating a state in which a heating unit is coupled with a head of a dispenser device for dental material according to example embodiments, FIG. 3 is an exploded perspective view of a head, a heating unit, and a cover of a dispenser device for dental material according to example embodiments, and FIG. 4 is a cross-sectional view viewed at a side of a head, a heating unit, and a cover of a dispenser device for dental material according to example embodiments.

Referring to FIGS. 2 through 4, the heating unit 50 of the dispenser device 1 according to example embodiment may be provided to the head 11 of the body 10.

In detail, the heating unit 50 may be coupled in a lower portion of the head 11. The heating unit 50 may be provided to the body 10 and may be configured to locally heat the capsule 20 by heating a portion of the capsule 20.

The heating unit 50 may include a film heater 51 configured to generate heat for heating the capsule 20 provided to the body 10 and a heat transferor 52 configured to transfer the heat generated from the film heater 51 to the capsule 20.

The film heater 51 may be formed using a flexible material in a shape of a thin plate. In general, a conventional dispenser device for dental material may include a heating pipe for heating the capsule 20 and may be configured to wrap a nicrome wire around the heating pipe. Accordingly, a volume of the conventional dispenser device may be enlarged. However, according to example embodiments, since the film heater 51 is provided in a shape of a thin plate using a bendable flexible material, spatial constraints for installing the heating unit 50 may be reduced and a structure of the body 10 may be simplified.

Also, the conventional dispenser device may employ a heating block for heating the capsule 20. In this case, due to a weight and a volume of the heating block, a use inconvenience may be accompanied. Further, it may be difficult to maintain the temperature of the capsule 20 to be uniform. On the contrary, using the film heater 51 according to example embodiments, it may be advantageous to maintain the temperature of the capsule 20 to be uniform and to enhance the use convenience compared to a case of using the heating block.

Referring to FIG. 3, the film heater 51 may be coupled at a lower portion of the body 10 in a bent state as a curved surface, and may be formed using a polyimide material. Polyimide (PI) is a polymer material having a transparency, a high heat-resistance and chemical resistance with a strong chain structure, an excellent mechanical property, an electrical characteristic, and a dimensional stability.

The film heater 51 may be formed in a structure which etched exothermic materials are present between PI films in the shape of thin plates. Heat may be generated in response to the electricity flowing in the exothermic material. An electrode portion 510 on which an electric wire is to couple with the film heater 51 may be provided on one side of the film heater 51. The film heater 51 may be electrically connected to the battery, the electric wire, and the like, through the electrode portion 510.

The electrode portion 510 may be electrically connected to the exothermic material present in the film heater 51, and may be formed using a conductive material through which electricity flows well. Further, although the electrode portion 510 may be provided in a cylindrical shape of FIG. 3, it is only an example. Accordingly, the electrode portion 510 may be provided in a variety of shapes.

A thin plate that forms the outer surface of the film heater 51 is formed using a PI material with an insulating property and thus, may prevent the external leakage of the electricity that flows in the exothermic material present in the film heater 51. As described above, according to example embodiments, it is possible to achieve the excellent insulation and the enhanced stability through the structure of the film heater 51.

The film heater 51 may generate the heat using the power supplied from the battery provided in the body grip 13, and may supply the generated heat to the heat transferor 52. The film heater 51 may control the heat generated from the exothermic material in the film heater 51 by controlling current and voltage supplied to the electrode portion 510 and accordingly, may control the heat that is transferred to the capsule 20 through the heat transferor 52. The caloric power of the film heater 51 may be controlled by adjusting the arrangement, amounts, etc., of the exothermic material provided in the film 51, so that the dental material, for example, resin and the like, in the capsule 20 may not be deformed and may be effectively melted within the range of current and voltage generally supplied to the electrode portion 510 of the film heater 51.

The heat transferor 52 may be provided between the capsule 20 and the film heater 51, and may transfer the heat generated from the film heater 51 to the capsule 20. That is, the film heater 51 may be in contact with the heat transferor 52, and may transfer the generated heat to the heat transferor 52 in a conductive manner.

Also, the heat transferor 52 may locally heat the capsule 20 in contact with a portion of the capsule 20. In detail, the heat transferor 52 may locally heat a lower portion of the capsule 20. For example, the heat transferor 52 may be formed using a metal material, for example, aluminum (Al), cupper (Cu), and the like, and may also be formed using different types of metal materials having an excellent thermal conductivity. It is only an example and thus, the example embodiments are not limited thereto.

The capsule combining groove 12 through which the capsule 20 is to couple with the body 10 may be dented on the head 11 of the body 10, and a heat transferor inserting hole 120 via which the heat transferor 52 is inserted into the body may be formed in the capsule combining groove 12 using a puncturing. The heat transferor 52 may be provided below the capsule 20, and the film heater 51 may be provided below the heat transferor 52.

A cover 60 may be included at an outside of the film heater 51. The cover 60 may detachably couple with the body 10 and may serve to cover the film heater 51. Also, the cover 60 may become in contact with lips of a patient while injecting the dental material into the patient and thus, may be formed using an insulating material.

Figure 5:
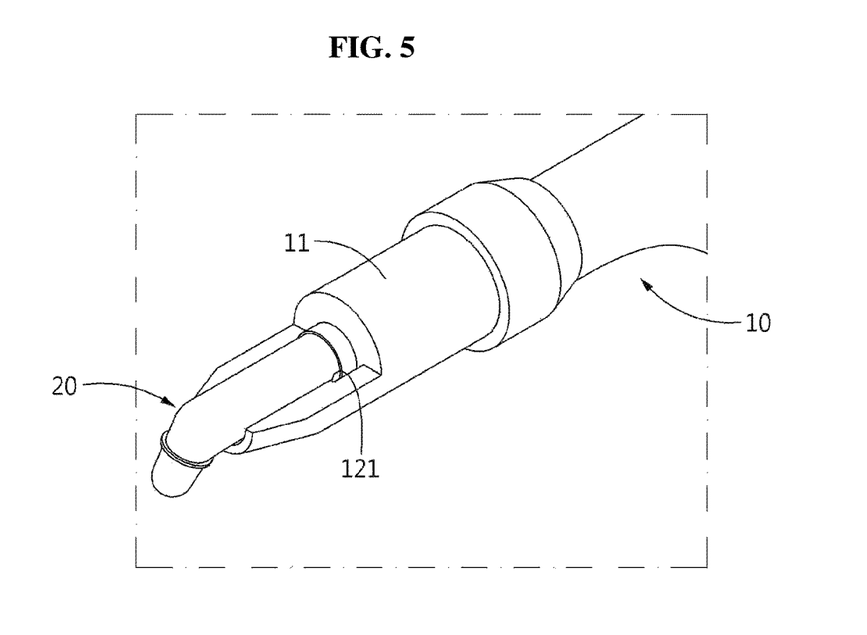
FIG. 5 is a view illustrating a state in which a capsule is coupled with a dispenser device for dental material according to some example embodiments.

FIG. 5 is a view illustrating a state in which a capsule is coupled with a dispenser device for dental material according to some example embodiments.

Referring to FIG. 5, the capsule 20 may detachably couple with the body 10 of the dispenser device 1 according to example embodiments.

A conventional capsule may be fixed within the body 10 instead of being detachably provided and thus, be entirely heated. That is, since a dental material accommodated in the conventional capsule may be deformed by heat and a power supply amount for heating the highly viscous dental material may increase, the battery efficiency may be degraded.

On the contrary, the capsule 20 of the dispenser device 1 according to example embodiments may couple with the body 10 to be detachable from the body 10. Further, when all of the dental materials accommodated in the capsule 20 are used, the capsule 20 may be separated from the body 10 and be replaced with a new capsule.

In detail, the capsule 20 may detachably couple with the capsule combining groove 12 formed on the head 11 of the body 10. A front end of the capsule 20 may be formed to be tilted at a predetermined angle, and a discharge hole (not shown) via which the dental material accommodated in the capsule 20 is discharged may be formed at the front end of the capsule 20. A rear end of the capsule 20 may couple with the piston 30 to be engaged at the front end of the piston 30. For example, the dental material accommodated in the capsule 20 may be resin. Since resin is a highly viscous material, a relatively great force may be required to extrude resin from the capsule 20.

The heating unit 50 capable of locally heating the highly viscous resin may be provided below the capsule 20. In response to a decrease in the viscosity of resin by heat, the rear end of the piston 30 may be pushed by the pressurizing portion 42 by pulling the actuator grip 41 toward the body grip 13. Here, since it is possible to locally heat the lower portion of the capsule 20, the internal pressure and temperature of the capsule 20 may uniformly increase.

Accordingly, it is possible to achieve the relatively high battery efficiency and to prevent the dental material accommodated in the capsule 20 from being deformed. In particular, since the capsule 20 is formed using a polymer material with a relatively excellent conductivity, the heat conducted from the heating unit 50 may be quickly transferred to the dental material in the capsule 20.

Also, the front end of the piston 30 is exposed at the outside of the head 11 by the pressurizing portion 42. Accordingly, the piston 30 may discharge the resin from the capsule 20 by pushing the resin accommodated in the capsule 20. A short step 121 may be formed on one side of the capsule combining groove 12. When the capsule 20 couples with the capsule combining groove 12 and the dental material is charged from the capsule 20 by the piston 30, the short step 121 may serve to prevent the capsule 20 from being pushed away from the head 11 by a force of the piston 30 pushing the dental material.

Hereinafter, an operation of the dispenser device 1 according to example embodiments will be described.

Initially, a user may grip the body grip 13. When the power is supplied from the battery (not shown) provided in the body grip 13 to the heating unit 50 and the capsule 20 starts being heated, the user may slowly pull the actuator grip 41 toward the body grip 13.

Once the user starts pulling the actuator grip 41, the pressurizing portion 42 integrally formed with the actuator grip 41 may pressurize the piston 30 while moving in a direction opposite to the actuator grip 41. That is, the piston 30 may move in a horizontal direction by a rotation of the actuator 40.

The capsule 20 may detachably couple with the head 11 formed at the front end of the body 10. The heat generated from the heating unit 50 may be transferred to the capsule 20 in a conductive manner to heat the dental material, for example, resin and the like, accommodated in the capsule 20. Once the pressurizing portion 42 pressurizes the piston 30 by a rotation of the actuator 40, the front end of the piston 30 may pressurize the rear end of the capsule 20 to thereby discharge, from the capsule 20, the dental material of which the viscosity is decreased. On the contrary, when all of the dental materials accommodated in the capsule 20 is used or when a necessary amount of dental materials is injected into a patient, the pressure applied to the actuator grip 41 may be released. Accordingly, the pressurizing portion 42 may not pressurize the piston 30 anymore and the piston 30 may return to an original position.

According to example embodiments, a film heater of a flexible material is used to heat a dental material having a relatively viscosity, instead of a conventional heating pipe and nicrome wire. Accordingly, it is possible to readily mount a heater regardless of a shape, a size, and a structure of a portion to which the heater is provided.

Also, according to example embodiments, it is possible to further advantageously maintain a temperature and to achieve an enhanced use convenience compared to a conventional method of using a heating block.

Also, according to example embodiments, since an inner structure of a dispenser device for dental material is simplified, a manufacture and processing may be conveniently performed.

Also, according to example embodiments, a pressure and a temperature of a dental material, such as resin and the like, may uniformly increase over time instead of instantaneously increasing by locally heating a lower end of a capsule, such as a resin capsule and the like, that accommodates the dental material. Also, the dental material, such as resin and the like, accommodated in the capsule may not be deformed.

Also, according to example embodiments, it is possible to relatively enhance the battery efficiency by locally heating a capsule that accommodates a dental material using a film heater.

Also, according to example embodiments, it is possible to readily attach and detach a capsule that accommodates a dental material, to and from a dispenser device.

Also, according to example embodiments, since a structure of a portion for heating a capsule is simplified, a risk of short-circuit and damage may be reduced, thereby further enhancing a stability.

Although a few example embodiments have been shown and described, the present disclosure is not limited to the described embodiments. Instead, it would be appreciated by those skilled in the art that changes may be made to these embodiments without departing from the principles and spirit of the disclosure, the scope of which is defined by the claims and their equivalents.

What is claimed is:

1. A dispenser device for dental material, the dispenser device comprising:
   a body having a head;
   a capsule for accommodating a dental material, wherein the capsule is configured to detachably couple with the body and have a curved outer surface;
   a piston extending in a first direction and configured to pressurize the capsule and to discharge the dental material from the capsule;
   an actuator configured to actuate the piston; and
   a heating unit provided in the head of the body, and configured to locally heat the capsule,
   wherein the head of the body includes:
   a capsule combining groove formed as an indentation, extending in the first direction and having a curved surface with which the capsule is to be in contact; and
   a heat transferor inserting hole formed in the capsule combining groove and passing through the curved surface of the capsule combining groove of the head in a second direction perpendicular to the first direction from an inner surface of the head to an outer surface of the head, the inner surface of the head corresponding to the curved surface of the capsule combining groove, and
   wherein the heating unit comprises:
   a film heater provided on the outer surface of the head and configured to generate heat for heating the capsule provided to the body; and
   a heat transferor having a curved upper surface and a lower surface and inserted into the heat transferor inserting hole in the second direction, configured to transfer the heat generated from the film heater to the capsule, and formed using a metal material,
   wherein the curved surface of the capsule combining groove corresponds to and surrounds the curved upper surface of the heat transferor,
   wherein the heat transferor is provided between the capsule and the film heater such that the curved upper surface of the heat transferor is in direct contact with a portion of the curved outer surface of the capsule and the curved surface of the capsule combining groove surrounding the curved surface of the heat transferor is in direct contact with another portion of the curved outer surface of the capsule when the capsule is coupled with the capsule combining groove of the body, and wherein the heat transferor is separated from the capsule and remains in the heat transferor inserting hole when the capsule is detached from the capsule combining groove of the body,
   wherein the film heater is formed using a flexible material in a shape of a thin plate,
   wherein the film heater is configured to couple with the body in a bent state as a curved surface,
   wherein the film heater is configured to contact the heat transferor, and to transfer heat to the heat transferor in a conductive manner, and the heat transferor is configured to locally heat the capsule, and
   wherein the heat transferor is provided below the capsule, and the film heater is provided below the heat transferor.

2. The dispenser device of claim 1, wherein the film heater includes polyimide films and an etched exothermic material between the polyimide films, and the dispenser device further comprises an electrode portion electrically connected to the material in the film heater.

3. The dispenser device of claim 1, wherein the heat transferor inserting hole is formed in the capsule combining groove by puncturing.

4. The dispenser device of claim 1, further comprising:
   a cover configured to cover a bottom of the film heater, and to detachably couple with the body.

5. The dispenser device of claim 1, wherein the dental material comprises resin.

6. A dispenser device for dental material, the dispenser device comprising:
   a capsule for accommodating a dental material, the capsule having a curved outer surface;
   a body having a head, the head comprising a capsule combining groove through which the capsule is configured to detachably couple with the body, the capsule combining groove formed as an indentation, extending in a first direction and having a curved surface with which the capsule is to be in contact, the head further comprising a heat transferor inserting hole formed in the capsule combining groove and passing through the curved surface of the capsule combining groove of the head in a second direction perpendicular to the first direction from an inner surface of the head to an outer surface of the head, the inner surface of the head corresponding to the curved surface of the capsule combining groove;
   a film heater provided on the outer surface of the head, and configured to locally heat at least a portion of the capsule;
   a heat transferor having a curved upper surface and a lower surface and inserted into the heat transferor inserting hole in the second direction, configured to transfer heat generated from the film heater to the capsule, and formed using a metal material; and
   a discharge unit configured to pressurize the capsule, and to discharge the dental material from the capsule,
   wherein the curved surface of the capsule combining groove corresponds to and surrounds the curved upper surface of the heat transferor,
   wherein the heat transferor is provided between the capsule and the film heater such that the curved upper surface of the heat transferor is in direct contact with a portion of the curved outer surface of the capsule and the curved surface of the capsule combining groove surrounding the curved surface of the heat transferor is in direct contact with another portion of the curved outer surface of the capsule when the capsule is coupled with the capsule combining groove of the body, and wherein the heat transferor is separated from the capsule and remains in the heat transferor inserting hole when the capsule is detached from the capsule combining groove of the body,
   wherein the film heater is formed using a flexible material in a shape of a thin plate,
   wherein the film heater is configured to couple with the body in a bent state as a curved surface,
   wherein the film heater is configured to contact the heat transferor, and to transfer heat to the heat transferor in a conductive manner, and the heat transferor is configured to locally heat the capsule,
   wherein the heat transferor is provided below the capsule, and the film heater is provided below the heat transferor, and wherein the film heater includes polyimide films and an etched material between the polyimide films, and the dispenser device further comprises an electrode portion electrically connected to the etched material in the film heater.

* * * * *